(12) United States Patent
Shorr et al.

(10) Patent No.: US 6,803,386 B2
(45) Date of Patent: Oct. 12, 2004

(54) PROSTACYCLIN DERIVATIVE CONTAINING COMPOSITIONS AND METHODS OF USING THE SAME FOR THE TREATMENT OF CANCER

(75) Inventors: Robert Shorr, Edison, NJ (US); Martine Rothblatt, Silver Spring, MD (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 10/047,802

(22) Filed: Jan. 16, 2002

(65) Prior Publication Data

US 2003/0166728 A1 Sep. 4, 2003

(51) Int. Cl.$^7$ ............................................. A61K 31/557
(52) U.S. Cl. ....................... 514/569; 514/617; 514/618; 514/619; 514/622; 514/729
(58) Field of Search ................................ 514/569, 617, 514/618, 619, 622, 729

(56) References Cited

U.S. PATENT DOCUMENTS

| | | | |
|---|---|---|---|
| 4,306,075 A | 12/1981 | Aristoff | 560/56 |
| 4,950,680 A | 8/1990 | Taylor et al. | 614/356 |
| 5,028,628 A | 7/1991 | Tadepalli et al. | 514/573 |
| 5,153,222 A | 10/1992 | Tadepalli et al. | 514/571 |
| 5,496,850 A | 3/1996 | Mutoh et al. | 514/468 |
| 5,545,671 A | 8/1996 | Schneider et al. | 514/573 |
| 5,877,215 A | 3/1999 | McClay et al. | 514/573 |
| 5,914,322 A | 6/1999 | Falk et al. | 514/54 |
| 6,054,486 A | 4/2000 | Crow et al. | 514/571 |
| 6,242,482 B1 | 6/2001 | Shorr et al. | 514/469 |

OTHER PUBLICATIONS

Hoper, Marius M. et al., "Prostanglandins Induce vascular endothelial growth factor in a human monocytic cell line and rat lungs via cAMP", abstract, Am. J. Respir. Cell Mol. Biol. 1997, 17 (6), 748–756.

Clapp, Lucie H., "Differential Effects of Stable Prostacyclin Analogs on Smooth Muscle Proliferation and Cyclic AMP Generation in Human Pulmonary Artery", Am. J. Respir. Cell Mol. Bio., vol. 26, pp. 194–201 (2002).

Shapiro, Shelley M. et al. "Primary pulmonary hypertension: improved long–term effects and survival with continuous intravenous epoprostenol infusion", abstract, J. Am. Coll. Cardiol. 1997, 30 (2), 343–349.

I–Ijima, Hiroaki et al., "Therapeutic efficacy of allergen–monomethoxy polyethylene glycol conjugates in the treatment of allergen–induced asthmatic guinea pigs", abstract, Int. Arch. Allergy Immunol. (1997), 113 (1–3), 323–325.

Gupta, Rajnish A. et al., "Prostacyclin–mediated activation of peroxisome proliferator–activated receptor Ō in colorectal cancer", PNAS, Nov. 21, 2000, vol. 57, No. 24, pp. 13,275–13,280.

Voelkel, Norbert F. et al., "Primary Pulmonary Hypertension between Inflammation and Cancer", Chest, 114,3, Sep., 1998 Supplement, pp. 225S–230S.

*Primary Examiner*—Rebecca Cook
(74) *Attorney, Agent, or Firm*—Watov & Kipnes, P.C.

(57) ABSTRACT

The present invention is directed to a pharmaceutical composition containing a cancer-treating effective amount of a class of prostacyclin derivatives, and a pharmaceutically acceptable carrier, and to kits and methods of employing the same for the treatment of cancer.

16 Claims, 3 Drawing Sheets

Compound of Formula II

FIG. 4

MMP Inhibitor

PROSTACYCLIN DERIVATIVE CONTAINING COMPOSITIONS AND METHODS OF USING THE SAME FOR THE TREATMENT OF CANCER

FIELD OF THE INVENTION

The present invention relates to prostacyclin derivative containing compositions, more specifically to prostacyclin derivative containing compositions suitable for use in the treatment of cancer.

BACKGROUND OF THE INVENTION

Prostaglandins are hormone-like substances found in the tissues and organs of the body. No other autocoids or hormones show more numerous or diverse biologically active effects than prostaglandins. They have been found to affect several body systems, including the central nervous, cardiovascular, gastrointestinal, urinary, and endocrine systems. Their effects on the endocrine system include stimulating the release of growth hormone by the pituitary gland, mediating the effects of luteinizing hormone on the ovary, stimulating the dissolution of the corpus luteum, and altering steroid hormone synthesis by the adrenal cortex. One prostaglandin compound has been found to be a powerful stimulant of uterine contractions and may prove useful for inducing labor.

Prostacyclin (a prostaglandin analog) is believed to act on the target cells via cellular surface receptors. These receptors are believed to be part of second messenger systems by which prostaglandin action is mediated. These compounds are known to be responsible in part to regulating a range of physiological responses including, for example, inflammation, blood pressure, blood clotting, fever, pain, induction of labor, and the sleep/wake cycle, and therefore are useful for preventing, controlling and treating a variety of diseases and pathological conditions in warm-blooded animals including humans.

Cancer is a disorder of cell growth that is typically characterized by invasion and destruction of surrounding healthy tissue by abnormal cells. Cancer cells typically arise from normal cells whose nature is permanently changed. They often multiply more rapidly than healthy body cells and do not seem subject to normal control by nerves and hormones. They may spread via the bloodstream or lymphatic system to other parts of the body, where they form metastatic clusters or nodules to produce further tissue damage (metastases). The ability of cancer cells to proliferate and metastasize is a major obstacle in the search for a treatment or cure. The mortality rate of cancer patients is closely linked to recurrence of metastatic cancer cells or malignant tumors. Certain classes of anticancer compounds are capable of inhibiting the spread of malignant tumors by inhibiting one or more steps of the process of tumor growth, migration and dissemination. Such compounds can improve the mortality rate among cancer patients.

The development of a metastasis represents the terminal stage of a complex series of events in which malignant cancer cells, spread to distant sites principally by way of the circulatory system. The first step of metastatic cascade usually involves cancer cell detachment from the primary tumor into newly formed tumor blood vessels. After cancer cell entry into the circulation, cancer cells interact with cellular and non-cellular components of the blood. Thereafter, circulating cancer cells attach to endothelial lining and penetrate into surrounding tissue. Although most cancer cells dispersed through this route die, a small number of cancer cells are able to complete all the steps of the metastatic cascade. Such cancer cells possess inherent biological properties that facilitate their survival, and are usually characterized by high invasiveness and motility. It is noted that the biochemistry underlying the process of the metastatic cascade is not entirely understood, however, it is believed that surface adhesion proteins, organelles or cell surface structures (e.g. invadopodia) and protease each may play a role in the cascade process. See, for example, Mueller S. C., Ghersi G., Akiyama S. K., Sang Q. X., Howard L., Pineiro-Sanchez M., Nakahara H., Yeh Y., Chen W. T. (1999) J. Biol. Chem. August 27, 274(35): 24947–52; and Chen W. T., Lee C. C., Goldstein L., Bernier S., Liu C. H., Lin C. Y., Yeh Y., Monsky W. L., Kelly T., Dai M. et al (1994) Breast Cancer Res. Treat. 31(2–3): 217–226.

One of these survival-enhancing properties may be the ability to interact with and attach to host platelets in the bloodstream, thus improving their potential to lodge in the microvasculature and adhere to the vascular endothelium lining. Alternatively, once lodged, cancer cells may initiate the formation of surrounding, protective platelet thrombi and enzymatic degradation of protein in the extracellular matrix, until extravasation or infiltration of the cancer cells through the blood vessel walls into surrounding tissue, is completed.

Anticoagulant therapy with aspirin, dipyridamole, heparin, and warfarin has been attempted in the hope of preventing metastasis. However, results to date have been inconclusive. On the other hand, prostaglandin compounds and analogs thereof including prostacyclin and derivatives thereof that are generally known potent anti-thrombogenic agents have been investigated with promising results for possessing potent inhibitory effects on tumor metastasis.

Studies have shown that prostaglandin compounds and analogs thereof function primarily by interfering with cancer cell-host interactions (such as cancer cell induced platelet aggregation, cancer cell adhesion to endothelial cells and sub-endothelial matrix, cancer cell induced endothelial cell retraction, protein degradation of the extracellular matrix, etc.) to produce such antimetastatic effects. Such compounds have also been found to exert protective effects in maintaining vascular and platelet homeostasis and preserving the integrity of the extracellular matrix to deter tumor growth, extravasation, and metastasis.

For example, U.S. Pat. No. 5,545,671 discloses prostacyclin derivatives Eptaloprost and Cicaprost as antimetastatic agents in combination with a physiologically compatible base and a cyclodextrin clathrate. U.S. Pat. No. 4,950,680 discloses the combination of a prostacyclin and a calcium channel blocker to prevent tumor induced platelet aggregation. U.S. Pat. No. 5,877,215 is directed to a method of increasing the cytotoxic effect of ionization radiation by the administration of a prostaglandin compound, especially prostaglandin $D_2$ or $\Delta^{12}$-prostaglandin $J_2$. U.S. Pat. No. 5,914,322 is directed to a topically applied treatment for skin cancers including a drug that inhibits prostaglandin synthesis, preferably a non-steroidal anti-inflammatory drug such as diclofenac. U.S. Pat. No. 5,496,850 discloses the use of a prostaglandin derivative, beraprost for the treatment of cancer.

Further studies performed to date also indicate that prostacyclin derivatives have a spectrum of activity against a wide variety of cancer types. Particularly, many of such prostacyclin derivatives have been shown to possess potent inhibitory effects on cancer cell metastasis in several differ- ent animal models including both experimental and spontaneous metastasis models. See, for example, Honn K V et al.: "Prostacyclin: a Potent Antimetastatic Agent", *Science* 212: 1270–72 (1981); Carteni et al.: "Biological activity of prostacyclin in patients with malignant bone and soft tissue tumors", *J. Cancer Res. Clin. Oncol.* 116 Suppl. Part 1: 631 (1990); Schneider et al.: "Antimetastatic Prostacyclin Analogs", *Drugs Future* 18:29–48 (1993); Daneker et al.: "Antimetastatic prostacyclins inhibit E-selectin mediated adhesion of colon carcinoma to endothelial cells", *Journal of Cellular Biochemistry Supplement* 19B:25 (1995); and Schirner et al.: "Inhibition of metastasis by Cicaprost in rats with established SMT2A mammary carcinoma growth", *Cancer Detection and Prevention,* 21(1): 44–50 (1997). In addition, prostacyclin derivatives have been shown to possess antiproliferative effects in cells and apoptosis effects in cancer cells.

It would therefore be a significant advance in the art of drug therapy, especially in the treatment of cancer, if pharmaceutical compositions employing prostacyclin derivatives could be employed for the inhibition of protein degradation including those caused by cancer cells, within the extracellular matrix of tissue and the like, and the treatment of cancer including, but not limited to, inhibiting metastasis of cancer cells, controlling cell proliferation in cancer cells, and promoting apoptosis in cancer cells.

SUMMARY OF THE INVENTION

The present invention is generally directed to pharmaceutical compositions comprising prostacyclin derivatives that possess pharmaceutical activity useful for the treatment of cancer and methods of using the same for the treatment of cancer in warm-blooded animals including humans. The present invention provides pharmaceutical compositions useful for the inhibition of protein degradation including those caused by cancer cells, within the extracellular matrix of tissue and the like, and the treatment of cancer including, but not limited to, inhibiting metastasis of cancer cells, controlling cell proliferation in cancer cells, and promoting apoptosis in cancer cells.

The pharmaceutical compositions of the present invention comprise, in combination with a pharmaceutically acceptable carrier, at least one prostacyclin derivative selected from compounds of Formula I and pharmaceutically acceptable salts and esters thereof,

I wherein:
n is 0 or 1;
$R_1$ is selected from the group consisting of O, N, S and C;
$R_2$ is an alkyl group having at least one carbon atom, preferably 1 to 6 carbon atoms;

X is selected from O or NH; and
R is selected from hydrogen or an alkyl group having at least one carbon atom, preferably 1 to 6 carbon atoms.

A particularly preferred prostacyclin derivative is represented by Formula II, and includes salts and esters thereof.

II

In one aspect of the present invention, the pharmaceutical composition comprises, in combination with a pharmaceutically acceptable carrier, a cancer-treating effective amount of at least one prostacyclin derivative selected from the compounds of Formula I and pharmaceutically acceptable salts and esters thereof.

In another aspect of the present invention, the pharmaceutical compositions may comprise a pharmaceutically acceptable carrier, and therapeutically effective amounts of at least one prostacyclin derivative selected from the compounds of Formula I and pharmaceutically acceptable salts and esters thereof, suitable for the inhibition of protein degradation including those caused by cancer cells, within the extracellular matrix of tissue and the like, and the treatment of cancer including, but not limited to, inhibiting metastasis of cancer cells, controlling cell proliferation in cancer cells, and promoting apoptosis in cancer cells.

In another particular aspect of the present invention, there is provided a method of treating warm-blooded animals including humans afflicted with cancer comprising administering to the warm-blooded animal a therapeutically effective amount of the pharmaceutical composition of the present invention.

In a further aspect of the present invention, there are provided methods of inhibiting metastasis of cancer cells, controlling cell proliferation in cancer cells, promoting apoptosis in cancer cells, inhibiting protein degradation such as caused by cancer cells in extracellular matrix of normal tissue, and the like, comprising administering to a warm-blooded animal including humans afflicted with cancer, a therapeutically effective amount of the pharmaceutical compositions of the present invention.

The present invention is further directed to a kit including pharmaceutical composition of the present invention and instructions for administration of the composition to warm-blooded animals, including humans.

BRIEF DESCRIPTION OF THE DRAWINGS

The following drawings are illustrative of embodiments of the invention and are not intended to limit the invention as encompassed by the claims forming part of the Application.

DETAILED DESCRIPTION OF THE INVENTION

The present invention is directed to novel pharmaceutical compositions useful for the treatment of cancer, comprising a class of prostacyclin derivatives, salts, and esters thereof, in combination with a pharmaceutically acceptable carrier. The cancer treatment may include, for example, inhibiting metastasis of cancer cells, controlling cell proliferation in cancer cells, promoting apoptosis in cancer cells, inhibiting protein degradation such as caused by cancer cells in extracellular matrix of normal tissue, and the like. The present invention relates to a method for treating cancer in warm-blooded animals including humans afflicted with cancer. The present invention also relates to kits for administering the present composition to warm-blooded animals, including humans.

Prostacyclin derivatives employed in the present invention have been observed to be useful antiproliferative and antimetastatic agents against cancer cells. The antimetastatic effects result primarily from the platelet antiaggregatory action and inhibitory effect on mechanisms causing cancer cell invasion and enzymatic protein degradation. The prostacyclin derivatives interfere with the capacity of metastasizing cancer cells to breakdown proteins including collagen, one of the main components of extracellular matrix in body tissue. As a result, the ability of cancer cells to penetrate the extracellular matrix is impaired by the administration of prostacyclin derivatives. The prostacyclin derivatives also can effectively interfere with the ability of cancer cells to interact with and attach to host platelets in the blood, which is a critical step in tumor metastasis. In this manner, the administration of such prostacyclin derivatives at least substantially compromises and inhibits the ability of cancer cells to invade the vascular endothelium.

Prostacyclin derivatives of the present invention have also been found to interfere with and disrupt established cancer cells adhering to the endothelium by preventing further formation of surrounding, protective platelet thrombi, thereby preventing eventual extravasation (migration through the endothelium into surrounding tissue mass). In addition to the antimetastatic effects, the prostacyclin derivatives have been observed to possess antiproliferative effects on cancer cells and to promote apoptosis in cancer cells.

The prostaglandin derivatives of the present invention are referred to by the standard, art-recognized system of nomenclature described by N. A. Nelson, J. Med. Chem. 17:911 (1974) for prostaglandins as 9-deoxy-PGF$_1$-type compounds, PGI$_2$ derivatives, or carbacyclins such as CBA$_1$ and CBA$_2$ derivatives.

The present invention encompasses prostacyclin derivatives represented by compounds of Formula I and pharmaceutically acceptable salts and esters thereof, wherein:
n is 0 or 1;
R$_1$ is selected from the group consisting of O, N, S and C;
R$_2$ is an alkyl group having at least one carbon atom, preferably 1 to 6 carbon atoms;
X is selected from O or NH; and
R is selected from hydrogen or an alkyl group having at least one carbon atom, preferably 1 to 6 carbon atoms.

Particularly preferred prostacyclin derivatives are represented by Formula II and pharmaceutically acceptable salts and esters thereof.

It is understood that the term "prostacyclin derivatives" represents compounds depicted in Formulas I and II, or a mixture comprising such compounds.

The pharmaceutically acceptable salts of the prostacyclin derivatives include salts derived from bases. Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulfates, with long chain halides, such as decyl, lauryl, myristyl, and stearyl chlorides, bromides, and iodides, and with aralkyl halides, such as benzyl and phenethyl bromides.

The prostacyclin derivatives of the present invention are conveniently prepared by methods the same as or analogous to those described in U.S. Pat. Nos. 4,306,075 and 5,153,222, each of which is incorporated herein by reference. A preferred method of preparing the prostacyclin derivatives of the present invention is illustratively shown and described in Example 4 hereinafter.

In one aspect of the present invention, the pharmaceutical composition comprises a cancer-treating effective amount of at least one prostacyclin derivative selected from the compounds of Formula I and pharmaceutically acceptable salts and esters thereof, in combination, with a pharmaceutically acceptable carrier.

In another aspect of the present invention, the pharmaceutical composition comprises a metastasis-inhibiting amount of at least one prostacyclin derivative selected from the compounds of Formula I and pharmaceutically acceptable salts and esters thereof, for inhibiting metastasis of cancer cells, in combination, with the pharmaceutically acceptable carrier.

In another aspect of the present invention, the pharmaceutical composition comprises a protein degradation-inhibiting effective amount of at least one prostacyclin derivative selected from the compounds of Formula I and pharmaceutically acceptable salts and esters thereof, for inhibiting protein degradation such as caused by metastasizing cancer cells, in combination, with the pharmaceutically acceptable carrier.

In another aspect of the present invention, the pharmaceutical composition comprises an antiproliferative effective amount of at least one prostacyclin derivative selected from the compounds of Formula I and pharmaceutically acceptable salts and esters thereof, for inhibiting cell proliferation in cancer cells, in combination with the pharmaceutically acceptable carrier.

In a further aspect of the present invention, the pharmaceutical composition comprises an apoptosis-promoting effective amount of at least one prostacyclin derivative selected from the compounds of Formula I and pharmaceutically acceptable salts and esters thereof, for promoting apoptosis in cancer cells, in combination with the pharmaceutically acceptable carrier.

The present invention further provides a method of treating warm-blooded animals including humans afflicted with cancer comprising administering to warm-blooded animals a cancer-treating effective amount of the present prostacyclin derivatives or the pharmaceutical composition of the present invention. As used herein a "cancer-treating effective amount" is defined as the amount sufficient to bring about therapeutic effects on the cancer to be treated in the warm-blooded animal. The precise amount that is considered effective for a particular therapeutic purpose will, of course, depend upon the specific circumstance of the warm-blooded animal being treated and the magnitude of the effect desired. Titration to effect may be used to determine proper dosage.

The present invention further provides a method of inhibiting metastasis in a warm-blooded animal including humans afflicted with cancer comprising administering to the warm-blooded animal a metastasis-inhibiting effective amount of the present prostacyclin derivatives or the pharmaceutical composition of the present invention. As used herein a "metastasis-inhibiting effective amount" is defined as the amount sufficient to bring about the slowing, halting or preventing of the onset of metastasis by the cancer being treated in the warm-blooded animal. The precise amount that is considered effective for a particular therapeutic purpose will, of course, depend upon the specific circumstance of the warm-blooded animal being treated and the magnitude of the effect desired.

The present invention further provides a method of inhibiting protein degradation such as caused by metastasizing cancer cells in a warm-blooded animal including humans afflicted with cancer comprising administering to the warm-blooded animal a protein degradation-inhibiting effective amount of the present prostacyclin derivatives or the pharmaceutical composition of the present invention. As used herein the term "protein degradation" shall refer to the degradation of all types of proteins including all proteins found in the extracellular matrix of tissues of warm-blooded animals. A common example of such proteins is collagen. As used herein a "protein degradation-inhibiting effective amount" is defined as the amount sufficient to bring about the slowing, halting or preventing of the onset of protein degradation such as that caused by the cancer being treated in the warm-blooded animal. The precise amount that is considered effective for a particular therapeutic purpose will, of course, depend upon the specific circumstance of the warm-blooded animal being treated and the magnitude of the effect desired.

The present invention further provides a method of promoting apoptosis in cancer cells within a warm-blooded animal including humans afflicted with cancer comprising administering to the warm-blooded animal an apoptosis-promoting effective amount of the present prostacyclin derivatives or the pharmaceutical composition of the present invention. As used herein an "apoptosis-promoting effective amount" is defined as the amount sufficient to bring about the onset of apoptosis or cell death in cancer cells treated in the warm-blooded animal. The precise amount that is considered effective for a particular therapeutic purpose will, of course, depend upon the specific circumstance of the warm-blooded animal being treated and the magnitude of the effect desired.

The present invention further provides a method of controlling cell proliferation in cancer cells within a warm-blooded animal including humans afflicted with cancer comprising administering to the warm-blooded animal an antiproliferative effective amount of the present prostacyclin derivatives or the pharmaceutical composition of the present invention. As used herein an "antiproliferative effective amount" is defined as the amount sufficient to bring about the slowing, halting or preventing of the onset of cell reproduction or proliferation in cancer cells treated in the warm-blooded animal. The precise amount that is considered effective for a particular therapeutic purpose will, of course, depend upon the specific circumstance of the warm-blooded animal being treated and the magnitude of the effect desired.

The present prostacyclin derivatives are employed as part of a pharmaceutical composition including a pharmaceutically acceptable carrier for the treatment of cancer including, but not limited to, inhibiting metastasis of the cancer, inhibiting protein degradation caused by metastasizing cancer cells, promoting apoptosis in cancer cells, controlling cell proliferation in cancer cells, and the like. The prostacyclin derivatives of the present invention employed for this purpose are typically administered in an amount of from 0.01 $\mu$g/kg/day to 500 mg/kg/day, preferably from about 0.01 $\mu$g/kg/day to 100 mg/kg/day. The dosage amount may vary depending upon a number of factors including, but not limited to, the type of cancer treated, the mode of administration, the patient profile (age, weight, etc.) and the like.

The pharmaceutical composition comprising at least one present prostacyclin derivative may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those known in the art of pharmaceutical formulation.

The pharmaceutical composition of the present invention may be administered by any suitable means including oral, inhalation in solid and liquid forms), rectal, topical, buccal (e.g. sublingual), parenteral (e.g. subcutaneous, intramuscular, intradermal, or intravenous) and transdermal administration, although the most suitable route in any given case will depend on the nature and severity of the condition being treated and on the nature of the particular form of prostacyclin derivative, or the pharmaceutically acceptable salt or ester thereof, which is being used. The present prostacyclin derivatives may be based for immediate release or extended release by the use of suitable pharmaceutical compositions or, particularly in the case of extended release, by the use of devices such as subcutaneous implants or osmotic pumps. The present prostacyclin derivatives may also be administered in the form of liposomes.

Formulations suitable for oral administration may be presented in discrete units, such as tablets, capsules, granules, lozenges, cachets, or powders, each containing a predetermined amount of the present prostacyclin derivative or a pharmaceutically acceptable salt or ester thereof; as a solution or a suspension in an aqueous or non-aqueous liquid; or as an oil-in-water or water-in-oil emulsion. Such formulations may be prepared by any suitable method of pharmacy that includes the step of bringing into association the present prostacyclin derivatives and a suitable carrier (which may contain one or more accessory ingredients).

Further exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art.

In general, the formulations of the invention are prepared by uniformly and intimately admixing the present prostacyclin derivative with a liquid or finely divided solid carrier, or both, and then, if necessary, shaping the resulting mixture. For example, a tablet may be prepared by compressing or molding a powder or granules containing the present prostacyclin derivatives, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising present prostacyclin derivative, or a pharmaceutically acceptable salt or ester thereof, in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the present prostacyclin derivative, or a pharmaceutically acceptable salt or ester thereof, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the prostacyclin derivative with water or a glycine buffer, and rendering the resulting solution sterile and isotonic with the blood. Injectable formulations according to the invention generally contain from about 0.1 to 5% w/v of present prostacyclin derivatives and are administered at a rate of about 0.1 ml/min/kg.

The present pharmaceutical composition may be administered subcutaneously in the form of a liquid reconstituted form a lyophilized powder that may additionally contain preservatives, buffers, dispersants, etc. Preferably, the prostacyclin derivatives can be reconstituted with a medium normally utilized for intravenous injection, e.g., preservative-free sterile water. Administration may be accomplished by continuous intravenous or subcutaneous infusion or by intravenous injection. For continuous infusion, the daily dosage can be added to normal saline or other solution and the solution infused by mechanical pump or by gravity.

Further exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Formulations suitable for rectal administration are preferably presented as unit dose suppositories that may contain, for example, a suitable non-irritating excipient, such as cocoa butter or synthetic glyceride esters, which are solid at ordinary temperatures, but liquify and/or dissolve in the rectal cavity to release the present prostacyclin derivatives. These formulations may be prepared by admixing the present prostacyclin derivative or a pharmaceutically acceptable salt or ester thereof, with one or more conventional solid carriers, for example, cocoa butter, and then shaping the resulting mixture into a suitable form.

Formulations suitable for topical application to the skin preferably take the form of an ointment, cream, lotion, paste, gel, spray, aerosol, or oil. Carriers that may be used include vaseline, lanoline, polyethylene glycols, alcohols, and combinations of two or more thereof. The present prostacyclin derivative is generally present at a concentration of from about 0.1 to 15% w/w, for example, from about 0.5 to 2% w/w. Further exemplary compositions for topical administration include a topical carrier such as Plastibase (mineral oil gelled with polyethylene).

Formulations for transdermal administration may be delivered by iontophoresis (see, for example, Pharmaceutical Research 3(6), 318, (1986)) and typically take the form of an optionally buffered aqueous solution of the present prostacyclin derivative, or of a salt or ester thereof. Suitable formulations comprise citrate or bis/tris buffer (pH 6) or ethanol/water and contain from about 0.1 to 0.2M active compound.

The present compositions may also be delivered through the oral cavity by sublingual and/or buccal administration. Molded tablets, compressed tablets or freeze-dried tablets are exemplary forms that may be used. Exemplary compositions include those formulating the present prostacyclin derivative with fast dissolving diluents such as mannitol, lactose, sucrose, and/or cyclodextrins. Also included in such formulations may be high molecular weight excipients such as celluloses (avicel). Such formulations may also include an excipient to aid mucosal adhesion such as hydroxypropyl cellulose (HPC), hydroxypropyl methylcellulose (HPMC), sodium carboxymethyl cellulose (SCMC), maleic anhydride copolymer (e.g. Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline that may contain, for example, benzyl alcohol or other suitable preservatives, absorption promoters to enhance bioavailability, and/or other solubilizing or dispersing agents such as those known in the art.

The effective amount of the composition of the present invention may be determined by one of ordinary skill in the art, and includes exemplary dosage amounts for an adult human from about 0.01 μg/kg to 500 mg/kg of body weight of the prostacyclin derivative of Formula I per day, preferably from about 0.01 μg/kg/day to 100 mg/kg/day, which may be administered in a single dosage or in the form of individual divided dosages, such as from 1 to 4 times per day. All cancers that are capable of metastasizing may be treated in accordance with the present invention including, but not limited to, cancers of the lung, liver, brain, pancreatic, kidney, prostate, breast, colon, and head-neck. It will be understood that the specific dosage level and frequency of dosage for any particular subject may be varied and will depend upon a variety of factors including the activity of the specific prostacyclin derivative, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to heart failure.

The present invention further provides kits comprising a cancer-treating effective amount of at least one prostacyclin derivative selected from compounds of Formula I and pharmaceutically acceptable salts and esters thereof, a pharmaceutically acceptable carrier, and instructions for administering the at least one prostacyclin derivative and pharmaceutically acceptable carrier to a warm-blooded animal including human. The effective amount being the same as described above. As used herein, the term "instructions" shall mean any FDA-mandated labeling, dosage instructions, or package inserts that relate to the administration of the prostacyclin derivatives of the present invention for the purpose of treating cancer. For example, instructions for administration of the prostacyclin derivative and the pharmaceutically acceptable carrier, may include, but is not limited to, indications for cancer, identification of specific symptoms of cancer that can be ameliorated by the present prostacyclin derivatives, and recommended dosages for warm-blooded animals including humans afflicted with cancer.

An assay developed for screening antimetastatic agents and determining the therapeutic response produced by such agents will be described herein. The corresponding assay has been designed to measure the changes in the invasive and adhesive capacity of the cancer cells brought about by the antimetastatic agent. It is known that cancer cells are capable of adhering to the basement membrane underlying blood vessel walls and entering through the corresponding adjacent connective tissues and extracellular matrix. See Liotta et al., Cancer Metastasis and Angiogenesis: An Imbalance of Positive and Negative Regulation, Cell 64, 327–336 (1991). Circulating cancer cells can adhere to the endothelium at metastatic sites and subsequently invade the extracellular matrix composed primarily of collagen, laminin, and fibronectin.

The assay for screening antimetastatic agents is comprised of a collagenous matrix comprising collagenous components including, but not limited to, Type I or Type VI collagen or denatured collagen such as gelatin to form a scaffold-matrix. The scaffold matrix is subsequently coated with blood-borne components such as fibronectin, laminin, and fibrin for promoting adherence of the cancer cells and thereafter, labeled with quench fluorescent dyes. During performance of the assay, cancer cells that are present, adhere, ingest and invade the labeled scaffold-matrix resulting in the release of highly fluorescent peptides. Generally, cancer cells include a specific cell structure typically comprised of tentacles or arms (i.e. invadopodia) which secrete specific digestive enzymes including seprase, dipeptidyl peptidase IV (DPPIV), membrane Type-1 matrix metalloproteinases, and the like, to breakdown the proteinaceous matrix. The fluorescence becomes visible only in the presence of these specific digestive enzymes produced by the cancer cells and increases in proportion to the activity of the digestive enzymes, thus providing a qualitative/quantitative measure of the invasiveness of the cancer cells. Other labeling methods including, but not limited to, the use of biotin, color dyes, and radioactive probes may also be used.

The forgoing discussion discloses and describes merely exemplary embodiments of the present invention. One skilled in the art will readily recognize from such discussion, and from the accompanying claims and examples, that various changes, modifications, and variations can be made therein without departing from the spirit and scope of the invention as defined in the claims forming part of the Application.

EXAMPLE 1

Protein Degradation Inhibiting Effects of the Prostacyclin Derivative Compound of Formula II on Human Amelanotic Melanoma Cells A study using test samples prepared from a Type I collagen matrix having cancer cells generated from a human amelanotic melanoma cell line (LOX) seeded thereon, was implemented to evaluate the collagen degradation inhibiting activity of the prostacyclin derivative compound of Formula II which is believed to adversely affect proteolytic enzymes by acting on receptors in the tumor cells. BATIMASTAT®, a hydroxamic acid metalloproteinase inhibitor, or "MMP inhibitor", known to be useful for inhibiting metastasis of tumors was used as a positive control. MMP inhibitor inhibits the activity of proteolytic enzymes after their release from the tumor cells, and therefore is believed to operate in a different manner then the compound of the present invention to collagen degradation. More details on MMP inhibitors can be found in Zucker et al, Critical appraisal of the use of matrix metalloproteinase inhibitors in cancer treatment, Oncogene (2000) 19, 6642–6650. The MMP inhibitor was obtained from British Biotech of Oxford, UK. The test compounds were assayed and analyzed to measure their collagen degradation inhibiting effects on the human amelanotic melanoma cells.

Collagen Degradation Inhibition Assay

As described herein, the assay utilizes a thin coating of collagen labeled with a fluorescent dye probe to form a scaffold collagen matrix, and cancer cells. The scaffold collagen matrix simulates the extracellular environment that is attacked by cancer cells during metastasis. The cancer cells attack the matrix by secreting proteolytic enzymes that break the collagen into peptide fragments. The peptide fragments release the fluorescent dye probe, and fluorescent light is emitted. The observed fluorescent light intensity correlates proportionally to the collagen degradation activity of the cancer cells.

Procedure

The cancer cells used in the test samples were generated from a human amelanotic melanoma cell line (LOX). A solution of a Type I collagen was prepared at a concentration of about 3.56 mg/ml. The collagen solution was used to form a coating of a monolayer of Type I collagen on a 96-well microtiter plate. The coating of Type I collagen on the microtiter plate was prepared by pipetting and polymerizing each well with a mixture of the Type I collagen solution, DMEM, and sterilized water in a volumetric ratio of 1:2:1. The collagen-coated microtiter plate was incubated at a temperature of about 37° C. for about 1 hour and air dried overnight. A stock fluorescent dye solution (Bodipy FL-C5 SE dye) having a concentration of about 5 mg/ml in dimethyl sulfoxide (DMSO) was obtained from Molecular Probes, Inc. of Eugene, Oreg. The fluorescent dye solution was diluted in a PBS buffer to a concentration of about 1.25 $\mu$g/ml. 100 $\mu$l of the diluted fluorescent dye solution was added to each well.

The microtiter plate containing the collagen coating and the dye was incubated at room temperature for a time sufficient to allow conjugation, typically for about 1 hour. The microtiter plate was washed five times with phosphate buffer solution (NaCl, 150 mM, $Na_2HPO_4$, 16 mM, $NaH_2PO_4$, 4 mM, pH 7.3) to remove excess reagents.

The LOX cells were cultured and incubated in a carbon dioxide incubator at 37° C. for 16 hours. The cells were seeded on the thin film of collagen matrix supported on a microtiter plate. The test compounds were added to the corresponding tissue cultures at dosages varying from about $10^{-12}$ to $10^{-3}$ M. The collagen degradation activity of the LOX cells was detected through the cleavage and release of fluorescent collagen peptides from the labeled collagen matrix film as described above. A positive fluorescence signal, $\Delta F$ indicates the presence of collagen degradation activity. The collagen degradation activity assay was performed four times (n=4) and its results are represented as mean±SEM values in FIGS. 1 and 2.

Figure 1:
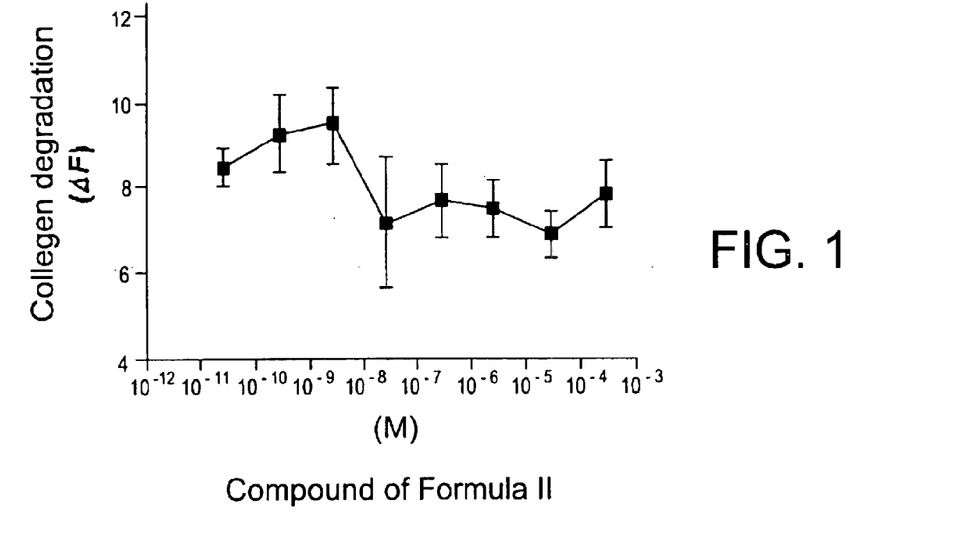
FIG. 1 is a graph showing collagen degradation inhibiting activity of the prostacyclin derivative compound of Formula II tested over a range of dosages.
Figure 2:
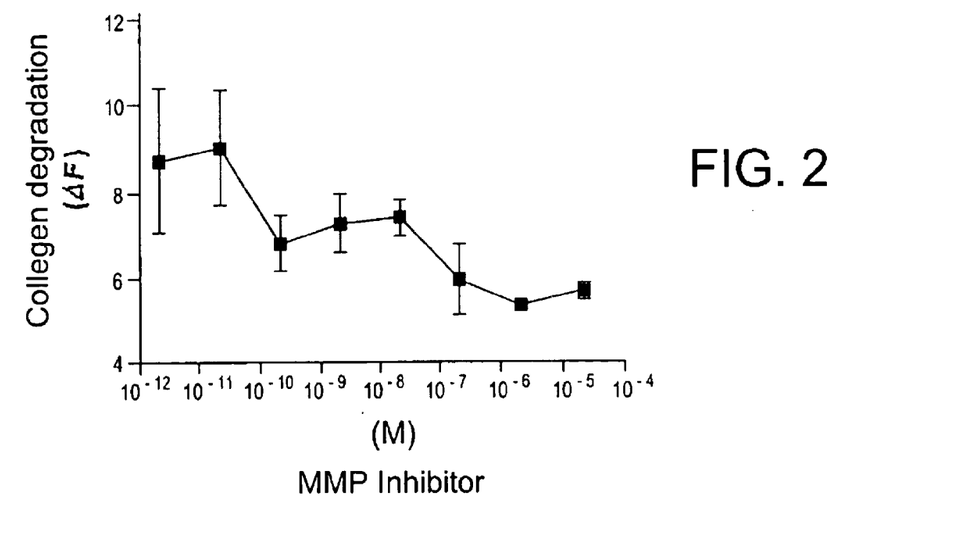
FIG. 2 is a graph showing collagen degradation inhibiting activity of a known hydroxamic acid inhibitor of matrix metalloproteinase, tested over a range of dosages.

Referring to FIG. 1, the graph shows the results of the collagen degradation inhibiting activity assay for the prostacyclin derivative compound of Formula II. The assay showed that the prostacyclin derivative compound of Formula II inhibited collagen degradation activity by LOX cells at a dosage as low as $2.5\times10^{-9}$ M ($IC_{50}=1\times10^{-8}$ M). Referring to FIG. 2, the graph shows the results of the collagen degradation activity assay for the MMP inhibitor. The assay showed that the MMP inhibitor inhibited collagen degradation activity by LOX cells at dosages greater than $10^{-10}$ M ($IC_{50}=2\times10^{-10}$ M).

Conclusion

The results of the collagen degradation inhibition assay indicate that the prostacyclin derivative compound of Formula II exhibited collagen degradation inhibiting effects over the range of dosages tested.

EXAMPLE 2

Cell Toxicity of the Prostacyclin Derivative Compound of Formula II on Human Amelanotic Melanoma Cells A study using test samples prepared from a Type I collagen matrix having cancer cells generated from a human amelanotic melanoma cell line (LOX) seeded thereon as employed in Example 1 was used to evaluate the dosage levels of prostacyclin derivative compound of Formula II necessary to achieve cell toxicity on human amelanotic melanoma cells. A similar test was conducted using the MMP inhibitor tested in Example 1.

Cell Toxicity Assay

The prostacyclin derivative compound of Formula II and the MMP inhibitor were assayed to evaluate their cell toxicity on the LOX cells. A live cell toxicity assay marketed as LIVE/DEAD Viability/Cytotoxicity Kit by Molecular Probes, Inc. of Eugene, Oreg., was obtained for the test. The assays were carried out in accordance with the manufacturers' instructions using the LOX cells. The LOX cells ($10^4$/well) were cultured and incubated in a carbon dioxide incubator at 37° C. overnight and then gently washed with PBS.

Calcein Am (2 $\mu$M), a fluorescent dye available from Molecular Probes, Inc. for staining live cells, was added to the LOX cells. The Calcein-stained LOX cells were incubated at room temperature for about an hour. The test compounds were added to the LOX cell cultures at dosages varying from about $10^{-12}$ to $10^{-3}$ M. The LOX cell cultures were incubated overnight. A positive fluorescence signal from the assay indicates the presence of viable cells in the test sample with the strength of the signal being proportional to the number of viable cells present.

Figure 3:
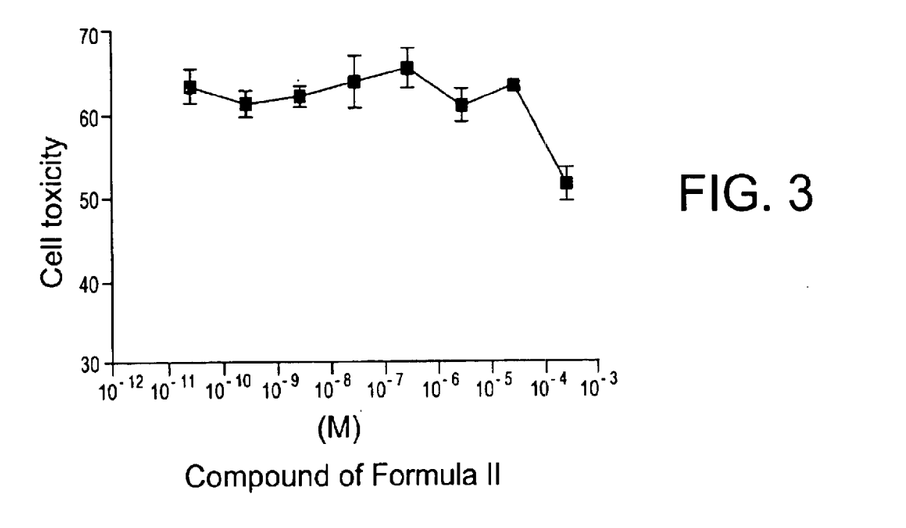
FIG. 3 is a graph showing cell toxicity levels of the prostacyclin derivative compound of Formula II tested over a range of dosages.
Figure 4:
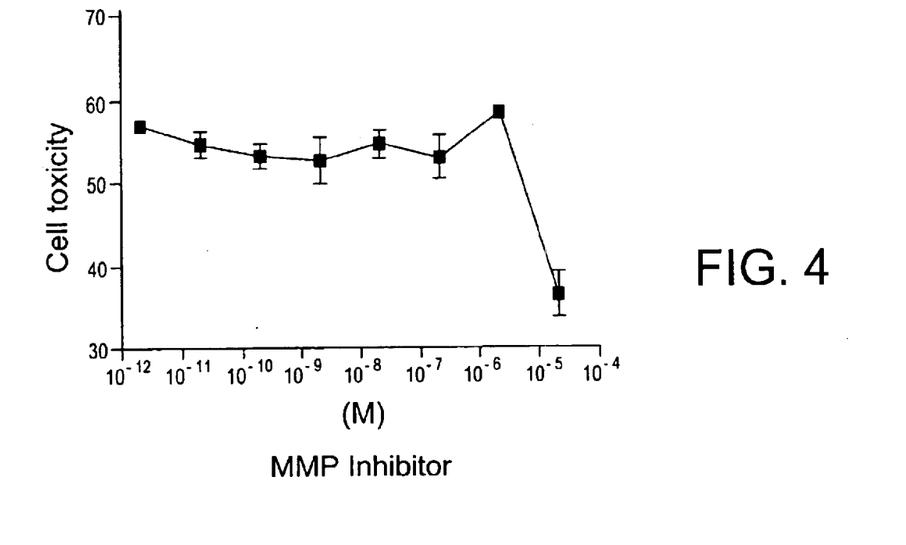
FIG. 4 is a graph showing cell toxicity levels of the known hydroxamic acid tested over a range of dosages.

The live cell toxicity assay was carried out four times (n=4) for each test compound. The results of the assay for each compound are represented as mean±SEM values in FIGS. 3 and 4. With reference to FIG. 3, the graph shows that the prostacyclin derivative compound of Formula II exhibited cell toxicity and inhibited cell viability at dosages of over $10^{-6}$ M. Referring to FIG. 4, the graph shows that the MMP inhibitor exhibited marked cell toxicity at dosages of over $10^{-6}$ M.

Conclusion

The results of the cell toxicity assay indicate that the prostacyclin derivative compound of Formula II exhibited cell toxicity at dosages much higher than necessary to inhibit collagen degradation.

EXAMPLE 3

Apoptosis-Promoting Effects of the Prostacyclin Derivative Compound of Formula II on Human Amelanotic Melanoma Cells A study using test samples prepared from a Type I collagen matrix having cancer cells generated from a human amelanotic melanoma cell line (LOX) seeded thereon as employed in Example 1 was used to evaluate the dosage levels of prostacyclin derivative compound of Formula II necessary to achieve apoptosis-promoting effects on human amelanotic melanoma cells. A similar test was conducted using the MMP inhibitor tested in Example 1.

Apoptosis Assay

The prostacyclin derivative compound of Formula II and the MMP inhibitor were assayed to evaluate their apoptosis-promoting effects on the LOX cells. An apoptosis assay marketed as Vybrant Apoptosis Assay Kit #4 from Molecular Probes, Inc., was obtained for the test. The assays were carried out in accordance with the manufacturers' instructions using the LOX cells. The LOX cells ($10^4$/well) were cultured and incubated in a carbon dioxide incubator at 37° C. overnight and then gently washed with PBS.

YO-PRO (2 $\mu$M), a fluorescent dye available from Molecular Probes, Inc., for staining apoptotic cells, was added to the LOX cells. The YO-PRO-stained LOX cells were incubated at room temperature for about 20 minutes. The test compounds were added to the second group of LOX cell cultures at dosages varying from about $10^{-12}$ to $10^{-3}$ M. The LOX cell cultures were incubated overnight. A positive fluorescence signal indicates the presence of apoptotic cells in the test sample with the strength of the signal being proportional to the number of apoptotic cells present.

Figure 5:
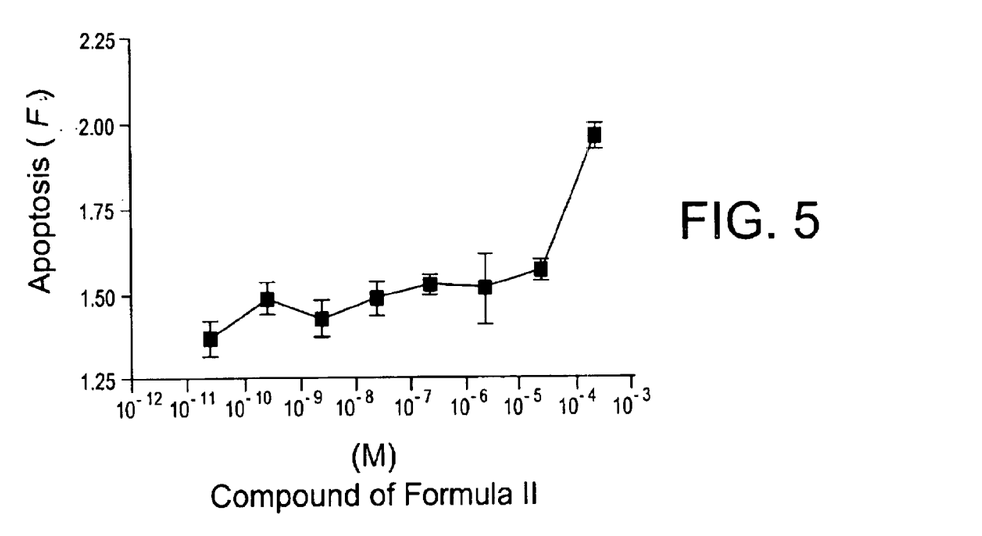
FIG. 5 is a graph showing apoptosis-promoting activity of the prostacyclin derivative compound of Formula II tested over a range of dosages.
Figure 6:
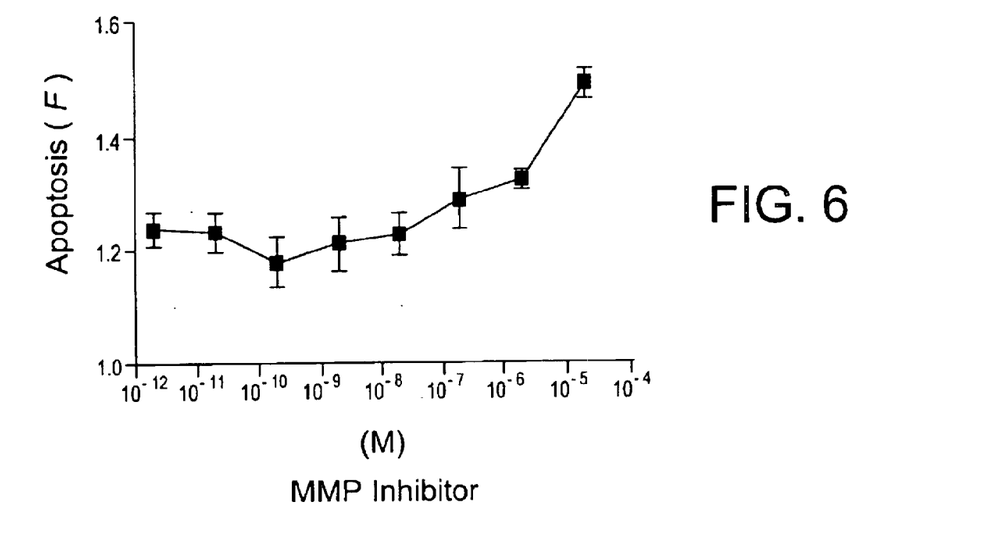
FIG. 6 is a graph showing apoptosis-promoting activity of the known hydroxamic acid tested over a range of dosages.

The apoptosis assay was performed four times (n=4) for each test compound. The results of the assay for each compound are represented as mean±SEM values in FIGS. 5 and 6. With reference to FIG. 5, the graph shows that the prostacyclin derivative compound of Formula II caused LOX cells to enter apoptosis at dosages over $10^{-6}$ M. The graph further shows a marked increase in the incidence of apoptosis induced by the prostacyclin derivative compound at dosages of over $10^{-4}$ M. Referring to FIG. 6, the graph shows that the MMP inhibitor caused the LOX cells to enter apoptosis at dosages of over $2\times10^{-6}$ M. The graph further shows a marked increase in the incidence of the MMP inhibitor-induced apoptosis at dosages of over $10^{-6}$ M.

Conclusion

The results of the apoptosis assay indicate that the prostacyclin derivative compound of Formula II exhibited apoptosis-promoting effects on human amelanotic melanoma cells over a range of dosages tested.

EXAMPLE 4

Synthesis of Compound of Formula II

The compound of Formula II, (i.e., 9-Deoxy-2',9α-methano-3-oxa-4,5,6-trinor-3,7-(1',3'-interphenylene)-13,14-dihydro-PGF$_1$), was prepared in the following manner.

Synthesis Procedure A 25 g of 3-methoxybenzyl alcohol (181 mmol) in 200 mL of methylene chloride were added to a solution comprising 29.6 g of imidazole (434 mmol, 2.8 eq.) in 1.0 L of methylene chloride. Upon complete dissolution, 32.7 g of t-butyldimethylsilyl chloride (TBDMSCl) (217 mmol, 1.2 eq.) were added in portions to the solution yielding a reaction mixture. The reaction mixture was stirred overnight at room temperature. The reaction mixture was then filtered and washed with water, and then with brine. The organic layer was separated, dried over MgSO$_4$, filtered, and then evaporated to yield 53 g of a clear yellow oil which was used in the next step without further purification.

Synthesis Procedure B

26.5 g of BuLi (414 mmol, 1.1 eq.) in 166 mL of hexane were added dropwise to a solution comprising 95 g of compound (2) (376 mmol) dissolved in 400 mL of hexane, at room temperature in the presence of argon. The resulting mixture was stirred at room temperature for about 2 hours, and then cooled in an ice bath. 54.6 g of allyl bromide (452 mmol) were added dropwise to the cooled mixture as stirring continued. The mixture was removed from the ice bath and allowed to warm to room temperature overnight. After stirring for about 24 hours, thin-layer chromatography (TLC) indicated 60% conversion, and the reaction was quenched with saturated NH$_4$Cl. The organic layer was separated and washed with brine, dried over MgSO$_4$, and filtered. The solvent was evaporated to yield a yellow oil which was used in the next reaction without further purification.

Synthesis Procedure C

128 g of tetrabutyl ammonium fluoride (TBAF) (489 mmol, 1.1 eq.) in 489 mL of tetrahydrofuran (THF) were added to a solution comprising 110 g of compound (3)(376 mmol) in 2.0 L of THF, to yield a reaction mixture. The reaction mixture was stirred at room temperature until the reaction was completed which was about 4 hours. The reaction was quenched by the addition of 500 mL of water. The organic layer was separated, washed with brine, dried over MgSO$_4$, and then filtered. The solvent was evaporated to yield an orange oil. The orange oil was purified by flash column chromatography on silica gel using 10–30% ethyl acetate in hexanes as the eluent. The fractions were evaporated to yield 24 g of a yellow oil (36% from 3-methoxybenzyl alcohol).

Synthesis Procedure D 24.2 g of dimethylsulfoxide (DMSO) (310 mmol) in 100 mL of $CH_2Cl_2$ were added dropwise to a solution comprising 20.6 g of oxalyl chloride (162 mmol, 1.2 eq.) in 250 mL of $CH_2Cl_2$, in the presence of argon at about −78° C. After 10 minutes, 24 g of compound (4)(135 mmol) in 100 mL of $CH_2Cl_2$ were added dropwise to the solution, to yield a reaction mixture. The reaction mixture was stirred for about 30 minutes at about −78° C. 68.3 g of triethylamine ($Et_3N$) (675 mmol, 5.0 eq.) were added to the reaction mixture. The reaction mixture was warmed to room temperature as stirring continued. The reaction was quenched with water, and washed with saturated $NH_4Cl$ solution, and then with brine. The organic layer was separated, dried over $MgSO_4$, and filtered. The solvent was evaporated to yield a brown oil which was purified by flash column chromatography on silica gel using 5% ethyl acetate in hexanes as the eluent. The fractions were evaporated to yield 20.5 g of a brown oil (86%).

Synthesis Procedure E

Compound (A) may be synthesized according to S. Takano et al., Chemistry Lett., 1987, p. 2017, the content of which is incorporated herein by reference. 2.24 mL of EtMgBr (6.72 mmol, 3M solution) was added to a solution comprising 1.6 g of compound (A) (6.72 mmol) in 10 mL of dry THF and gently refluxing in the presence of argon. After the addition was complete, the resulting solution was refluxed for about 20 minutes.

The refluxed solution was cooled to 0° C. in the presence of argon. A solution comprising 1.183 g of compound (5) (6.72 mmol) in 10 mL of THF (dried over molecular sieves) was added dropwise to the refluxed solution under stirring to yield a reaction mixture. After the complete addition, the reaction mixture was allowed to warm to room temperature, and was stirred for about 2 to 3 hours. The reaction mixture was then cooled to 0° C., diluted with saturated $NH_4Cl$ solution, concentrated, extracted with 25 mL of ethyl acetate four times, and dried over $MgSO_4$. The solvent was distilled out in vacuo to yield a crude product. The crude product (2.65 g) was purified by flash chromatography using 10–30% ether in hexane on silica gel to yield 1.45 g of compound (6) in the form of a colorless oil (52%).

Synthesis Procedure F 1.32 g of pyridinium chlorochromate (PCC) (6.12 mmol) was added to a solution comprising 1.27 g of alcohol (6) (13.07 mmol) in 20 mL of dry $CH_2Cl_2$. The resulting mixture was stirred at room temperature. As PCC slowly dissolved into the mixture, the color of mixture turned orange-black after approximately 5 minutes. Stirring was maintained for about 3 hours thereafter. The mixture was diluted with 100 mL of ether and filtered through a plug of silica gel to yield a solid. The solid was washed with 50 mL of ether 3 times. The solvent was removed to yield a crude product. The crude product (1.3 g) was purified by flash chromatography using 10% ether in hexane on silica gel to yield 900 mg of a light yellow oil (71%).

8

Synthesis Procedure G
Step I: Preparation of Reagent

Compound (B) may be synthesized according to D. S. Mathre et al., J. Org. Chem. 1991, Vol. 56, p. 751; P. Beak, Org. Synth., 1997, p. 23, the content of which is incorporated herein by reference. 1.08 g of compound (B) (4.26 mmol) was dissolved in 30 mL of anhydrous toluene in the presence of argon. 0.357 g of trimethylboroxine (C) (2.84 mmol) was added dropwise to the solution. The solution was stirred at room temperature. A white solid was separated out after about 3 to 4 minutes. After stirring for about 30 minutes, toluene was distilled out at atmospheric pressure. 20 mL of dry toluene were added, and then distilled out. The distillation process was repeated 2 more times thereafter. The solution of reagent in toluene was allowed to cool in the presence of argon.

Step II: Reduction

A solution comprising 0.88 g of ketone (7) (2.14 mmol) in 20 mL of dry THF, was dried over molecular sieves for about 2 hrs, and then added to the above prepared reagent solution. The resulting solution was cooled to about −30° C. ($CH_3CN$, $CO_2$) in the presence of argon. 1.07 mL of borane-methylsulfide complex (10.71 mmol) was added dropwise into the solution with stirring. The solution was stirred at about −30° C. for about 1 hour. The reaction was quenched with 10 mL of methanol, diluted with 100 mL of ether, washed successively with saturated $NH_4Cl$, $NaHCO_3$ solution, and brine, dried over $MgSO_4$, and concentrated in vacuo to yield a crude product (2.3 g). The crude product was purified by flash chromatography using 10% ether in hexanes on silica gel to yield 770 mg of compound (8) in the form of a colorless oil (87%).

Synthesis Procedure H 0.337 g of t-butyldimethylsilyl chloride (TBDMSCI) (2.23 mmol) and 0.335 g of imidazole (4.65 mmol) were added at room temperature in the presence of argon to a solution comprising 0.770 g of compound (8) (1.86 mmol) in 20 mL of dimethylformamide (DMF). The mixture was stirred at room temperature for about 3 to 4 hours. After the reaction was quenched with saturated $NH_4Cl$, the reaction mixture was extracted with 50 mL of ether 3 times. The combined ether extracts were dried over $MgSO_4$, and concentrated in vacuo to yield a crude oil. The crude oil was purified by chromatography using 5% ether in hexane on silica gel to yield 860 mg of compound (9) in the form of a colorless oil (88%).

Synthesis Procedure I
Step I: Complex Formation 0.840 g of compound (9) (1.59 mmol) was dissolved in 15 mL of dry $CH_2Cl_2$ in the presence of argon. 0.653 g Of $CO_2(CO)_8$ (1.91 mmol) was added to the solution and stirred in the presence of argon at room temperature. Carbon monoxide was permitted to escape from the solution, and the solution turned dark brown after about 5 minutes. The solution was stirred for about 30 minutes at room temperature.

Step II: Pauson Khand Cyclization

$CH_2Cl_2$ was distilled out from the solution prepared immediately above to yield a complex. The complex was dissolved in 50 mL of dry $CH_3CN$, and the solution was refluxed for about 2 hours in the presence of argon. The solvent was subsequently distilled from the solution to yield a crude product. The crude product was dissolved in ether and quickly passed through a short column of neutral alumina to yield 850 mg of a light brown oil (96%).

Synthesis Procedure J 0.850 g of compound (10) (1.53 mmol) was dissolved in 50 mL of absolute ethanol. 0.020 g of anhydrous $K_2CO_3$ and 0.550 g of Pd/C (10%, wet) were added to the solution to yield a reaction mixture. The reaction mixture was hydrogenated for about 13 hours under a pressure of about 20 psi. The reaction mixture was filtered through celite and concentrated in vacuo to yield a crude product. The crude product (800 mg) compound (11) was purified by chromatography using 10–30% ether in hexane on silica gel to yield 440 mg of a colorless oil (67%).

Synthesis Procedure K

A solution comprising 0.430 g of compound (11) in 95% ethanol was cooled to about −10° C. 6 mL of 10% NaOH and 0.080 g of $NaBH_4$ were added to the solution and the mixture was stirred for about 1 hour at a temperature of about −10° C. An additional equivalent of $NaBH_4$ (0.080 g) was added, and stirring was maintained at about −10° C. for about 5 hours. After carefully quenching with glacial acetic acid, the solvent was removed under reduced pressure to yield an oil. The oil was dissolved in ethyl acetate, washed successively with aqueous $NaHCO_3$ and brine, dried over $MgSO_4$, and then concentrated in vacuo to yield 430 mg of a colorless oil (98%), which has a single spot on thin-layer chromatography (TLC) to yield a compound (12). Further purification was not required.

Synthesis Procedure L 20 mg of p-TsOH was added to 400 mg of compound (12) (0.93 mmol) dissolved in 10 mL of methanol. The resulting solution was stirred at room temperature until the TLC indicated the completion of the reaction, which was about 2 hours. The solvent was removed in vacuo. The residue was dissolved in $CH_2Cl_2$, washed with saturated $NaHCO_3$, dried over $MgSO_4$, and then concentrated in vacuo to yield a crude product. The crude product was purified by silica gel column chromatography using 30% ether in hexanes as an eluent to yield 250 mg of compound (13) (78%).

Synthesis Procedure M 1.1. mL of n-BuLi (1.72 mmol)(1.6 M in hexanes) was added dropwise to a solution comprising 0.28 g of diphenylphosphine (1.5 mmol) in 8 mL of anhydrous THF stirred in the presence of argon at a temperature of about −20° C., to yield a reaction mixture. The reaction mixture was then warmed to room temperature (20° C.). A solution comprising 0.17 g of compound (13) (0.49 mmol) in 0.6 mL of dry THF was added dropwise to the reaction mixture. The reaction mixture was then heated and refluxed for about 3 hours (TLC shows starting material). The reaction mixture was then cooled to a temperature of about −20° C. 0.37 g of diphenylphosphine (1.96 mmol) was added to the reaction mixture, followed by dropwise addition of 1.5 mL of n-BuLi (2.38 mmol)(1.6M in hexanes) in the presence of argon. After completing addition, the reaction mixture was warmed to a temperature of about 20° C., and then refluxed for about 18 hours. TLC showed 80–90% conversion to compound (14). The reaction mixture was then cooled to −5° C. An aqueous solution of NaCl containing 5% conc. HCl was added dropwise to quench the reaction. The reaction mixture was extracted with 20 mL of ethyl acetate 3 times, and the combined organic layers were washed with brine, dried over $Na_2SO_4$, filtered, and concentrated to yield a crude product. The crude product was purified by silica gel column chromatography (50% EtOAc/Hex. as eluent) to yield 0.12 g of the crude product (75%) (22 mg of starting diol was recovered).

Synthesis Procedure N

A suspension comprising 0.12 g of compound (14) (0.37 mmol), 0.56 g of chloroacetonitrile (7.4 mmol), and 0.51 g of $K_2CO_3$ (3.7 mmol) in 15 mL of dry acetone was refluxed for about 20 hours in the presence of argon. The reaction mixture was then cooled to room temperature, and 0.5 g of celite was added thereto. After the reaction mixture was filtered, the solvent was removed under reduced pressure to yield a crude product. The crude product was purified by silica gel column chromatography using 1:1 EtOAc/hexanes as eluent to yield 0.12 g of the crude product (95%) of compound (15).

Synthesis Procedure O

Aqueous KOH (0.4 g, 7.12 mmol, water 1.2 ml, 35% solution) was added dropwise to a stirred solution comprising 0.072 g of nitrile compound (15) (0.21 mmol) in 4 mL of methanol, to yield a reaction mixture. The reaction mixture was refluxed for about 3 hours. The reaction mixture was then cooled to a temperature of about 10° C., and dilute aqueous HCl was added to attain a pH of 8. The solvent was removed in vacuo. 20 mL of ethyl acetate and 10 mL of aqueous NaCl solution were added, and the reaction mixture was acidified by the addition of 2% HCl to attain a pH within the range of about 2 to 3. The reaction mixture was extracted with 20 mL of ethyl acetate twice. The combined ethyl acetate extracts were washed with brine, dried over $Na_2SO_4$, and concentrated under reduced pressure to yield a crude product. The crude product was purified by silica gel column chromatography using a dichloromethane solution containing 3% methanol and 0.1% acetic acid as an eluent to yield 0.076 g of the crude product compound (16) (i.e., the compound of Formula II (95%)).

What is claimed is:

1. A method of treating a cancer selected from the group consisting of lung, liver, brain, pancreatic, kidney, prostate, breast, colon and head-neck cancer in a warm-blooded animal comprising administering to the warm-blooded animal afflicted with said cancer a cancer-treating effective amount of a pharmaceutical composition comprising at least one prostacyclin derivative selected from the compound of Formula I or a pharmaceutically acceptable salt or ester wherein:

n is 0 or 1;

X is selected from O or NH;

$R_1$ is selected from the group consisting of O, N, S and C;

$R_2$ is an alkyl group having at least one carbon atom, and
R is selected from H or an alkyl group having at least one carbon atom, and a pharmaceutically acceptable carrier.

2. The method of claim 1 comprising administering said at least one prostacyclin derivative in a dosage amount of from about 0.01 μg/kg/day to 500 mg/kg/day to said warm-blooded animal.

3. The method of claim 1 comprising administering said at least one prostacyclin derivative in a dosage amount of from about 0.01 μg/kg/day to 100 mg/kg/day to said warm-blooded animal.

4. The method of claim 1 comprising administering said pharmaceutical composition intravenously to said warm-blooded animal.

5. The method of claim 1 comprising administering said pharmaceutical composition subcutaneously to said warm-blooded animal.

6. The method of claim 1 comprising administering said pharmaceutical composition by inhalation to said warm-blooded animal.

7. The method of claim 1 comprising administering said pharmaceutical composition orally to said warm-blooded animal.

8. The method of claim 1 wherein said warm-blooded animal is a human.

9. A method of inhibiting metastasis in a warm-blooded animal afflicted with a cancer selected from the group consisting of lung, liver, brain, pancreatic, kidney, prostate, breast, colon and head-neck cancer, said method comprising administering to the warm-blooded animal a metastasis-inhibiting effective amount of a pharmaceutical composition comprising at least one prostacyclin derivative selected from the compound of Fomula I or a pharmaceutically acceptable salt or ester wherein;
n is 0 or 1;
X is selected from O or NH;
$R_1$ is selected from the group consisting of O, N, S and C;
$R_2$ is an alkyl group having at least one carbon atom, and
R is selected from H or an alkyl group having at least one carbon atom, and a pharmaceutically acceptable carrier.

10. The method of claim 9, wherein said warm-blooded animal is a human.

11. A method of inhibiting protein degradation caused by cancer cells in a warm-blooded animal afflicted with a cancer selected from the group consisting of lung, liver, brain, pancreatic, kidney, prostate, breast, colon and head-neck cancer, said method comprising administering to the warm-blooded animal a protein degradation-inhibiting effective amount of a pharmaceutical composition comprising at least one prostacyclin derivative selected from the compound of Fomula I or a pharmaceutically acceptable salt or ester wherein:
n is 0 or 1;
X is selected from O or NH;
$R_1$ is selected from the group consisting of O, N, S and C;
$R_2$ is an alkyl group having at least one carbon atom, and
R is selected from H or an alkyl group having at least one carbon atom, and a pharmaceutically acceptable carrier.

12. The method of claim 11, wherein said warm-blooded animal is a human.

13. A method of promoting apoptosis in cancer cells in a warm-blooded animal afflicted with a cancer selected from the group consisting of lung, liver, brain, pancreatic, kidney, prostate, breast, colon and head-neck cancer, said method comprising administering to the warm-blooded animal an apoptosis-promoting effective amount of a pharmaceutical composition comprising at least one prostacyclin derivative selected from the compound of Fomula I or a phamaceutically acceptable salt or ester wherein:
n is 0 or 1;
X is selected from O or NH;
$R_1$ is selected from the group consisting of O, N, S and C;
$R_2$ is an alkyl group having at least one carbon atom, and
R is selected from H or an alkyl group having at least one carbon atom, and a pharmaceutically acceptable carrier.

14. The method of claim 13, wherein said warm-blooded animal is a human.

15. A method of controlling cell proliferation of cancer cells in a warm-blooded animal afflicted with cancer selected from the group consisting of lung, liver, brain, pancreatic, kidney, prostate, breast, colon and head-neck cancer, said method comprising administering to the warm-blooded animal an antiproliferative effective amount of a pharmaceutical comprsing at least one prostacyclin derivative selected from the compound of Fomula I or a pharmaceutically acceptable salt or ester wherein:

n is 0 or 1;

X is selected from O or NH;

$R_1$ is selected from the group consisting of O, N, S and C;

$R_2$ is an alkyl group having at least one carbon atom, and

R is selected from H or an alkyl arou having at least one carbon atom, and a pharmaceutically acceptable carrier.

16. The method of claim 15, wherein said warm-blooded animal is a human.

* * * * *